US008673566B2

(12) United States Patent
Ramirez-Arcos et al.

(10) Patent No.: US 8,673,566 B2
(45) Date of Patent: Mar. 18, 2014

(54) METHOD FOR DETECTION OF STAPHYLOCOCCUS EPIDERMIDIS

(75) Inventors: Sandra M. Ramirez-Arcos, Ottawa (CA); Cherie Cameron, Kanata (CA)

(73) Assignee: Canadian Blood Services, Ottawa, Ontario ( * ) Notice: Subject to any disclaimer, the term of this patent is extended or adjusted under 35 U.S.C. 154(b) by 410 days.

(21) Appl. No.: 11/584,871

(22) Filed: Oct. 23, 2006

(65) Prior Publication Data

US 2008/0268432 A1 Oct. 30, 2008

Related U.S. Application Data

(60) Provisional application No. 60/728,754, filed on Oct. 21, 2005.

(51) Int. Cl.
*C12Q 1/68* (2006.01)
*C07H 21/04* (2006.01)

(52) U.S. Cl.
USPC .... 435/6.12; 536/24.3; 536/24.32; 536/24.33

(58) Field of Classification Search
None
See application file for complete search history.

(56) References Cited

U.S. PATENT DOCUMENTS

2003/0022343 A1* 1/2003 Heidler et al. ................. 435/196
2003/0049636 A1* 3/2003 Bergeron et al. .................. 435/6
2004/0248148 A1* 12/2004 Horgen et al. ..................... 435/6

FOREIGN PATENT DOCUMENTS

WO WO01/23604 A2 4/2001

OTHER PUBLICATIONS

Greco et al. GenBank GI:61696945 [online] Mar. 28, 2005 [retrieved on Feb. 1, 2009] retrieved from: http://www.ncbi.nlm.nih.gov/entrez/viewer.fcgi?db=nuccore&id=61696945 (2 pages).*
Gerke et al. GenBank GI:2978429 (aka accession No. U43366) [online] Mar. 19, 1998 [retrieved on Feb. 1, 2009] retrieved from: http://www.ncbi.nlm.nih.gov/entrez/viewer.fcgi?db=nuccore&id=2978429 (4 pages).*
Arciola et al. In catheter infections by *Staphylococcus epidermidis* the intercellular adhesion (ica) locus is a molecular marker of the virulent slime-producing strains. J Biomed Mater Res 59:557-562 (2002).*
GenBank accession No. CP000029 [online] Jan. 13, 2005 [retrieved on Aug. 25, 2009] retrieved from http://www.ncbi.nlm.nih.gov/sviewer/viewer.fcgi?57636010:OLD04:5991470 (pp. 1, 195 and 858).*
Yin et al. Real-time reverse transcriptase-polymerase chain reaction (RT-PCR) for measurement of cytokine and growth factor mRNA expression with fluorogenic probes or SYBR Green I. (Immunology and Cell Biology 79:213-221 (2001)).*

Dreier, Jens, et al., "Two Novel Real-Time Reverse Transcriptase PCR Assays for Rapid Detection of Bacterial Contamination in Platelet Concentrates," Journal of Clinical Microbiology, pp. 4759-4764 (2004).
Fadda, Daniela, et al., "Characterization of divIVA and other Genes Located in the Chromosomal Region Downstream of the dcw Cluster in *Streptococcus pneumoniae*," Journal of Bacteriology, pp. 6209-6214 (2003).
Mohammadi, Tamimount, et al., "Real-Time Amplification of HLA-DQA1 for Counting Residual White Blood Cells in Filtered Platelet Concentrates," Transfusion, 44:1314-1318 (2004).
Pinho, Mariana and Errington, Jeff, "A divIVA Null Mutant of *Staphylococcus aureus* Undergoes Normal Cell Division," FEMS Microbiology Letters, 240:145-149 (2004).
Ramirez-Arcos, Sandra, et al., "*Enterococcus faecalis* divIVA: An Essential Gene Involved in Cell Division, Cell Growth and Chromosome Segregation," Microbiology, 151:1381-1393 (2005).
Ramirez-Arcos, Sandra, et al., "Development of Molecular Assays for the Detection and Identification of Bloodborne Bacteria in Platelets," (Abstract), Transfusion 44 (SP45):46A; at the Annual Meeting of the American Association of Blood Banks, Baltimore, USA, Oct. 23-26, 2004.
Ramirez-Arcos, Sandra, et al., "Validation of the BacT/Alert System to Implement Bacterial Detection in Apheresis Platelets in Canada," 25th Meeting of the Canadian Society for Transfusion Medicine. Niagara in the Lake, Canada. May 13-16, 2004; presented at the 25th Meeting of the Canadian Society for Transfusion Medicine.
Rohde, Holger, et al., "Detection of Virulence-Associated Genes Not Useful for Discriminating Between Invasive and Commensal *Staphylococcus epidermidis* Strains from a Bone Marrow Transplant Unit," Journal of Clinical Microbiology, pp. 5614-5619 (2004).
Zhang, Yue-Qing, et al., "Genome-based Analysis of Virulence Genes in a Non-Biofilm-Forming *Staphylococcus epidermidis* Strain (ATCC 12228)," Molecular Microbiology, 49(6):1577-1593 (2003).
Arciola, C.R. et al., Acta Orthrop Scand, 74(5):617-621 (2003). "Occurrence of ica genes for slime synthesis in a collection of *Staphylococcus epidermidis* strains from orthopedic prosthesis infections."
Gill, S. et al., Journal of Bacteriology, 187(7):2426-2438 (2005). "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis* Strain."
de Silva et al., "The *ica* Operon and Biofilm Production in Coagulase-Negative Staphylococci Associated with Carriage and Disease in a Neonatal Intensive Care Unit," Journal of Clinical Microbiology, Feb. 2002, vol. 40 (2): 382-388.

* cited by examiner (Continued)

*Primary Examiner* — Samuel Woolwine
(74) *Attorney, Agent, or Firm* — Wolf, Greenfield & Sacks, P.C.

(57) ABSTRACT

A method for detecting the bacteria *Staphylococcus epidermidis* includes isolating DNA from a biological sample suspected of containing the bacteria. The method further includes subjecting the DNA to a Polymerase Chain Reaction (PCR) amplification method utilizing at least one primer derived from a cell division gene. The method may further include characterizing an indicator of a *Staphylococcus epidermidis* phenotype of interest. The method additionally includes detecting the bacterium *Staphylococcus epidermidis* by visualizing the product of the polymerase chain reaction. Amplification products of cell division genes and virulence genes are also provided.

16 Claims, 4 Drawing Sheets

Figure 2A. Comparison of divIVA sequences from *Staphylococcus epidermidis* and *Staphylococcus aureus*

```
SedivIVA   361  --------------------TTCCGCTCTCGTTTCCGTATGCTTGTTGAAGCACAACTT
SadivIVA   361  --------------------TTTAGATCGCGTTTCCGTATGTTAGTTGAAGCGCAATTA SedivIVA   421  GACTTACTCAAAAGTGAAGATTGGGATTACTTACTCAATTATGATTTAGACGCCGAGCAA
SadivIVA   421  GACTTATTAAAAACCGAAGATTGGGATTACTTGTTGAATTATGATTTAGACGCTGAACAA SedivIVA   481  GTGACATTAGAAGATATTCATCATCTTCATGATAATGATTTGACACCTGAAGAACGTGCA
SadivIVA   481  GTGACGCTTGAAGATATTCATCATTTGCATGAAAATGATTTAAAGCCAGATGAAGTTGCA SedivIVA   541  AT-----------------
SadivIVA   541  G------------------

SedivIVA= Staphylococcus epidermidis divIVA
SadivIVA= Staphylococcus aureus divIVA
Black boxes highlight residues that are conserved while gray boxes show related
nucleotides.
```

Figure 2B. Comparison of *icaA* sequences from *Staphylococcus epidermidis* and *Staphylococcus aureus*

```
SeicaA   719  --------------------GCTCTATGCTGGATGTTAGTGCCTGAAACTATAGGTGGTT
SaicaA   719  --------------------GCCATGTGTTGGATGTTGGTTCCAGAAACATTGGGAGGTC SeicaA   779  TATGGAAACAAAGGGTTCGATGGGCTCAAGGCGGCCATGAAGTACTTTAAGAGACTTTT
SaicaA   779  TTTGGAAGCAACGCCGTGAGATGGGCTCAAGGCGGCACACGAAGTATTACTACGAGACTTTT SeicaA   839  GGCCAACAATTAAAACTAAGAAATTATCACTATATATTTTAATGTTTGAACAAATCGCAT
SaicaA   839  TTAGCACAATGAAAACGAAAAGGTTTCCTTTATATATTTTCATGTTTGAGCAAATCATCT SeicaA   899  CGATTACATGGGTCTACATCG-------------------
SaicaA   899  CAATTTTATGGGTATATATAG-------------------

SeicaA= Staphylococcus epidermidis icaA
SaicaA= Staphylococcus aureus icaA
Black boxes highlight residues that are conserved while gray boxes show related
nucleotides.
```

Figure 3A. Multiplex QPCR assay using the QuantiTect Multiplex
PCR No ROX kit and the MX4000 system (Strategene)
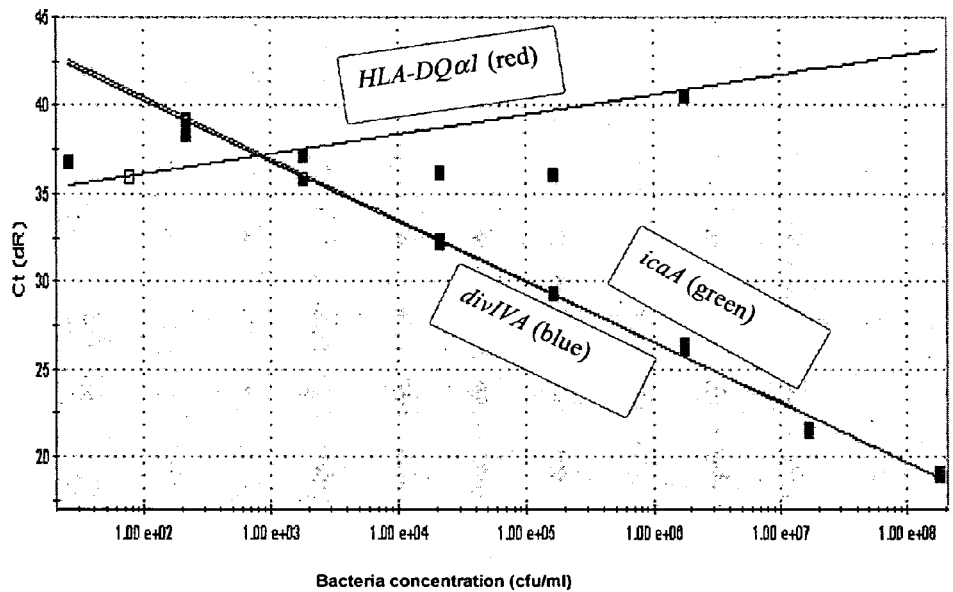
Figure 3B. QPCR amplification of *Staphylococcus epidermidis divIVA*
showing a limit of detection of $10^2$ cfu/ml
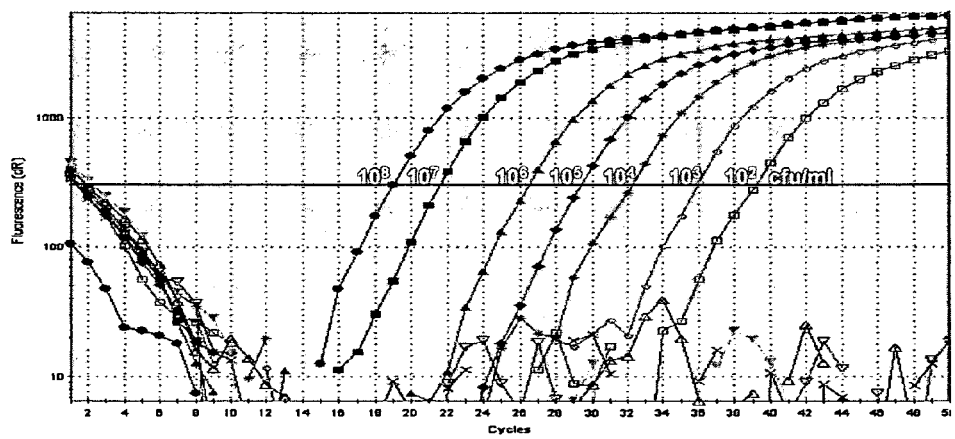

Figure 4. Multiplex QPCR amplification of *Staphylococcus epidermidis* *divIVA*, *icaA* and *DQa1* showing a limit of detection of $10^2$ cfu/ml
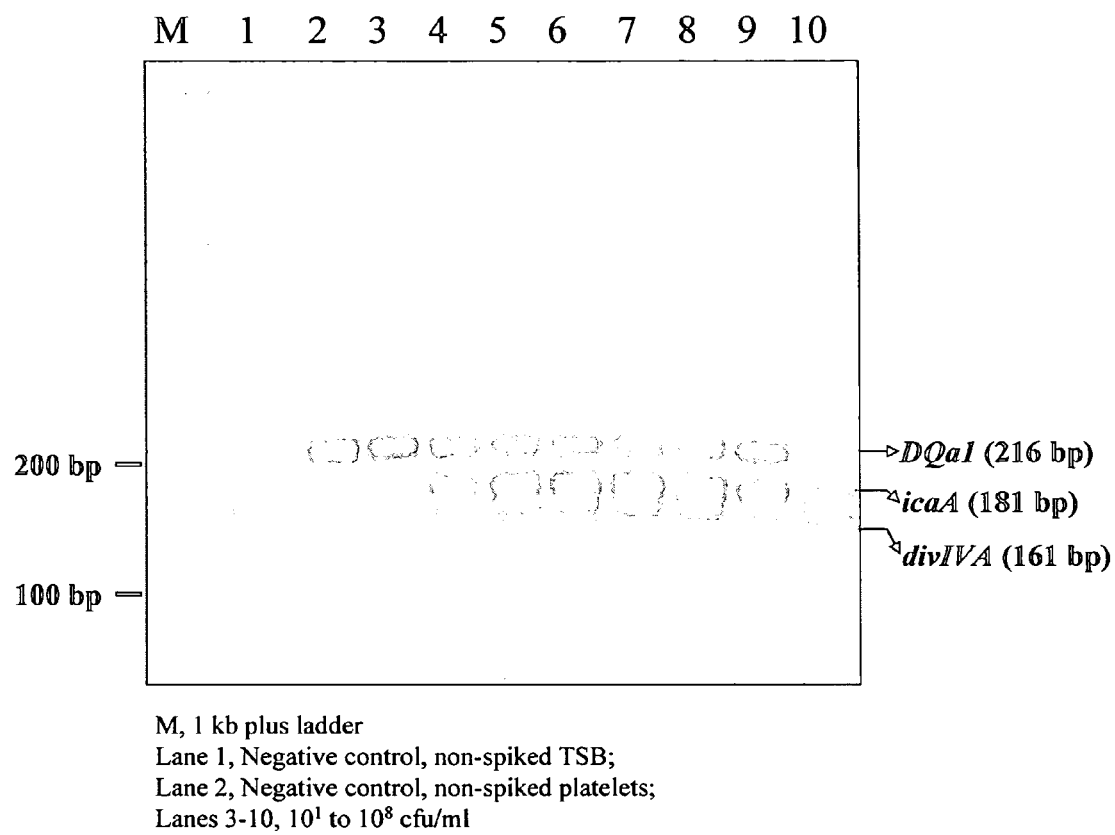
M, 1 kb plus ladder
Lane 1, Negative control, non-spiked TSB;
Lane 2, Negative control, non-spiked platelets;
Lanes 3-10, $10^1$ to $10^8$ cfu/ml

METHOD FOR DETECTION OF STAPHYLOCOCCUS EPIDERMIDIS

CROSS REFERENCE TO RELATED APPLICATION

This application claims priority under 35 U.S.C. §119 based on U.S. Provisional Application No. 60/728,754 filed Oct. 21, 2005, the disclosure of which is herein incorporated by reference.

FIELD OF THE INVENTION

The present invention relates generally to a method for detecting *Staphylococcus epidermidis* bacterial contamination. More specifically, the present invention provides a method for molecular detection of *Staphylococcus epidermidis*, and includes nucleic acid products for achieving the same.

BACKGROUND

Bacterial contamination of blood products continues to be the major microbiological cause of transfusion-associated morbidity and mortality. Platelets are the most susceptible blood product to bacterial contaminants. Furthermore, platelets are generally stored aerobically for up to 5 days at 20 to 24° C., allowing a wide variety of bacteria to grow.

Conventional methods for the detection of bacteria in blood components involve culturing and identification by morphological, biochemical, and immunological characteristics. Several methods have been designed to detect bacterial contamination in platelets with different ranges of sensitivity and specificity. The automated culture system BacT/ALERT™ has been implemented for routine testing of bacterial contamination of platelets in Canada and by many blood suppliers from the United States and Europe. Although BacT/ALERT™ can detect <10 colony forming units (cfu)/ml of bacteria, this system detects microorganism growth by tracking $CO_2$ production via a calorimetric sensor-and-detection system, and thus provides non-specific detection of bacterial presence. Microorganisms multiply in a select media, generating $CO_2$ and as $CO_2$ increases, a calorimetric sensor is indicated, typically in a bottle. Measuring reflected light, the system monitors and detects color changes in the sensor, and algorithms are used to analyze the data to determine positivity.

According to this system, changes in the sensor are permanent and visible to the unaided eye. Despite its high sensitivity, this system lacks specificity, requires a high volume of platelets for testing, and involves long incubation periods for bacterial detection.

Likewise, a commercially available kit for nucleic acid detection of microbial contaminants known as Bug's n' Beads™ is described in International Publication WO 98/51693 published Nov. 19, 1998. Although Bugs n' Beads™ provides a different approach to nucleic acid detection, it does so in a time consuming manner, while requiring a generous sample size.

Other molecular genetic techniques have been employed for detecting bacterial contamination at sensitive levels for some bacterial species. Dreier et al. (Journal of Clinical Microbiology, 2004, Vol. 42, p. 4759-4764) describe a Real-Time Reverse Transcriptase Polymerase Chain Reaction (PCR) Assay for detecting bacterial contamination in platelets. This methodology targeted a 290-bp product of the 23S rRNA as a broad target in the detection of a diversity of bacterial species. However, the sensitivity of this methodology was marginal, even with the employment of 7 ml of platelet-rich plasma as a starting material. As a result, further optimization achieving a larger nucleic acid input was required.

Since the maximum storage period for platelets is 5 days, and bacterial contamination of platelets is of growing concern in donor blood products, there remains an eminent need for a rapid, sensitive and efficient method for detecting and quantifying bacterial contamination in platelet samples.

SUMMARY

A novel method for detecting, qualifying and quantifying *Staphylococcus epidermidis* contamination in a sample suspected of containing the same is herein provided. According to a preferred embodiment, the present subject matter provides a molecular detection method and compositions used therein, for detecting *Staphylococcus epidermidis* in a blood sample. More preferably, embodiments include methods and compositions specific for detecting *Staphylococcus epidermidis* in a platelet sample. Methods consistent with the present subject matter may employ novel primers and probes for detecting *Staphylococcus epidermidis*. The primer and probe sets employed in accordance embodiments of the present application may include oligonucleotide primers and a fluorescent probe for the molecular detection methods of designed to detect and/or characterize preferred gene targets and/or genetic markers specific to the species *Staphylococcus epidermidis*.

In addition to identifying a novel target for *Staphylococcus epidermidis* detection, a target and corresponding indicator of potential virulent forms of *Staphylococcus epidermidis* virulence are provided. Accordingly, the present subject matter further comprises nucleic acid products for detecting, qualifying and quantifying the presence of *Staphylococcus epidermidis* in a biological sample. An additional embodiment as herein provided includes a multiplex QPCR method for simultaneously screening for genetic markers for determining the presence and qualifying the potential virulence of *Staphylococcus epidermidis* thereof. Such an embodiment includes use of a plurality of primer and probe sets specific to the genetic markers identified in accordance with the present subject matter.

According to a preferred embodiment, there is provided a novel detection method for the rapid and highly sensitive detection of *Staphylococcus epidermidis* in platelets. The sensitivity of this method provides for accurate bacterial detection with a preferred platelet sample size of 200 µl whereby detection of $>/=10^2$ cfu/ml can be achieved in a minimal time period, and preferably within approximately three hours. As a result, rapid, highly sensitive detection and discrimination of a very important bloodborne pathogen is achieved by the methodology herein provided.

In accordance with one embodiment of the present subject matter there is provided a method for detecting *Staphylococcus epidermidis*, said method comprising: isolating DNA from a sample suspected of containing *Staphylococcus epidermidis*; subjecting the DNA to polymerase chain reaction amplification utilizing at least one primer of a first primer pair, wherein said at least one primer is specific for a region of a divIVA gene of *Staphylococcus epidermidis*; and detecting *Staphylococcus epidermidis* by visualizing the product of the polymerase chain reaction.

In accordance with another embodiment of the present subject matter there is provided a method for simultaneously detecting and characterizing *Staphylococcus epidermidis*, said method comprising isolating DNA from a sample suspected of containing *Staphylococcus epidermidis*; subjecting the DNA to a multiplex polymerase chain reaction amplification utilizing a least one primer from a first primer pair having specificity to a divlVA gene target of *Staphylococcus epidermidis* and at least one primer from a second primer pair having specificity to an icaA gene target of *Staphylococcus epidermidis*; and screening for products of the polymerase chain reaction for each of the divlVA gene target and icaA gene target of *Staphylococcus epidermidis* to obtain an indication of the presence and phenotype of *Staphylococcus epidermidis* in the sample.

In another embodiment of this subject matter, a primer set for detecting *Staphylococcus epidermidis* using polymerase chain reaction, comprising: a first primer comprising a base sequence (SEQ ID NO: 1) 5'TTCCGCTCTCGTTTCCGT3' or a function variant thereof and a second primer comprising a base sequence (SEQ ID NO:2) 5'ATTGCACGTTCTTCAGGTGT3' or a function variant thereof. A primer comprising SEQ ID NO:1 or a functional variant thereof is preferably a forward primer. A primer comprising SEQ ID NO:2 or a functional variant thereof is preferably a reverse primer.

In another embodiment of this subject matter provides a primer set for characterizing *Staphylococcus epidermidis* using polymerase chain reaction to obtain an indication of a virulence phenotype, comprising: first primer comprising a base sequence (SEQ ID NO: 4) 5'GCTCTATGCTGGATGTTAGTGCCTGA3' or a function variant thereof; and a second primer comprising a base sequence (SEQ ID NO: 5) 5'CGATGTAGACCCATGTAATCGATGCG3' or a function variant thereof. A primer comprising SEQ ID NO:4 or a functional variant thereof is preferably a forward primer. A primer comprising SEQ ID NO: 5 or a functional variant thereof is preferably a reverse primer.

In an additional exemplary embodiment, a primer and probe set for detecting *Staphylococcus epidermidis* using polymerase chain reaction, comprising: a forward primer comprising a base sequence (SEQ ID NO: 1) 5'TTCCGCTCTCGTTTCCGT3'; a reverse primer comprising a base sequence (SEQ ID NO: 2) 5'ATTGCACGTTCTTCAGGTGT3'; and
a probe comprising a base sequence (SEQ ID-NO: 3)-5'-FAM-TGCTTGTTGAAGCACAACTTGACTTACTCA-BHQ1-3' or functional variants of any of SEQ ID NOs: 1, 2 or 3.

In an additional exemplary embodiment, a primer and probe set for detecting *Staphylococcus epidermidis* using polymerase chain reaction, comprising: a primer and probe set for charactering *Staphylococcus epidermidis* using polymerase chain reaction to obtain an indication of a virulence phenotype, comprising: a forward primer comprising a base sequence (SEQ ID NO: 4) 5'GCTCTATGCTGGATGTTAGTGCCTGA3' and a reverse primer comprising a base sequence (SEQ ID NO: 5) 5'CGATGTAGACCCATGTAATCGATGCG3'; and a probe comprising a base sequence (SEQ ID NO: 6) 5'-HEX-TGGAAACAAAGGGTTCGATGGGCTC-3'-BHQ2 or functional variants of any of SEQ ID NOs: 4, 5 or 6.

According to a preferred embodiment of the present subject matter, DNA amplification and/or detection by polymerase chain reaction (PCR) may be quantitative polymerase chain reaction (QPCR).

In accordance with a further embodiment, a method for determining the potential virulence of a strain of *Staphylococcus epidermidis* is herein provided. This embodiment includes isolating DNA from a sample suspected of containing *Staphylococcus epidermidis*; subjecting the DNA to PCR amplification utilizing a primer pair comprising at least one primer selected from one of (SEQ ID NO: 4) 5'GCTCTATGCTGGATGTTAGTGCCTGA3' and (SEQ ID NO: 5) 5'CGATGTAGACCCATGTAATCGATGCG3' base sequences, or a functional variant thereof; and determining virulence properties of the bacterium *Staphylococcus epidermidis* by visualizing the product of the PCR.

In another exemplary embodiment, a primer set for determining *Staphylococcus epidermidis* virulence using PCR includes a first primer comprising a first base sequence of (SEQ ID NO. 4) 5'GCTCTATGCTGGATGTTAGTGCCTGA3' and a second primer comprising a base sequence (SEQ ID NO. 5) 5'CGATGTAGACCCATGTAATCGATGCG3' or a functional variant thereof.

In an additional exemplary-embodiment consistent with the invention, probe(s) for detecting an indicator of potential virulence of a *Staphylococcus epidermidis* isolate are also provided. One such probe of the present invention comprises a base sequence (SEQ ID NO: 6) 5'-HEX-TGGAAACAAAGGGTTCGATGGGCTC-3'-BHQ2. A primer/probe set may be provided including a probe of SEQ ID NO: 6 together with a forward primer comprising a first base sequence of (SEQ ID NO: 4) 5'GCTCTATGCTGGATGTTAGTGCCTGA3' and a reverse primer comprising a base sequence(SEQ ID NO: 5) 5'CGATGTAGACCCATGTAATCGATGCG3', or functional variants of any of the above, where said primer/probe set may be employed for detecting an indicator of potential virulence of a *Staphylococcus epidermidis* isolate using PCR.

According to a preferred embodiment, the primer/probe sets of the present invention may be employed in a multiplex PCR for detecting and qualifying the potential virulence of *Staphylococcus epidermidis* isolates in samples of interest. It is further contemplated that primers and/or probes of the present invention may be employed in a multitude of multiplex PCR methodologies for simultaneous detection and qualification of *Staphylococcus epidermidis* isolate and other biological contaminants of interest.

In accordance with another aspect of the present subject matter there is provided a kit for detecting *Staphylococcus epidermidis*, said kit comprising a first primer and probe set corresponding to one or more gene targets for detecting *Staphylococcus epidermidis* using polymerase chain reaction; and a set of instructions for adapting said kit for detecting one or more indicators of *Staphylococcus epidermidis* in a sample suspected of containing the same using polymerase chain reaction.

According to a preferred embodiment of the present invention, there is provided a novel detection method for the rapid and highly sensitive detection of *Staphylococcus epidermidis* in platelets. The sensitivity of this method provides for accurate bacterial detection with a platelet sample of merely 200 μl whereby detection of $\geq/=10^2$ cfu/ml can be achieved within approximately three hours. As a result, rapid, highly sensitive detection and discrimination of a very important bloodborne pathogen is achieved by a novel methodology of the present invention.

We can specifically detect *Staphylococcus epidermidis* by sampling 200 μl of platelets instead of the 4 ml need by the BacT/ALERT system. Furthermore, the present subject matter provides a method for both quantitative and qualitative detection of this important bacteria. High sensitivity is achieved by detecting $\geq/=10^2$ cfu/ml of *Staphylococcus epidermidis* within approximately three hours instead of the 20 hours required by the BacT/ALERT system. This unique method permits the rapid detection and discrimination of a very important bloodborne pathogen.

BRIEF DESCRIPTION OF THE DRAWINGS

The accompanying drawings, which are incorporated in and constitute a part of the specification, illustrate embodiments of the invention and, together with the description, explain the invention. In the drawings.

FIG. 2A illustrates a comparison of the gene region that is amplified with the QPCR primers for divIVA between *Staphylococcus epidermidis* (SEQ ID NO: 10) and *Staphylococcus aureus* (SEQ ID NO: 11) according to an embodiment of the subject matter herein described.

FIG. 2B illustrates a comparison of the gene region that is amplified with the QPCR primers for icaA between *Staphylococcus epidermidis* (SEQ ID NO: 12) and *Staphylococcus aureus* (SEQ ID NO: 13) according to an embodiment of the subject matter herein described.

FIG. 3A illustrates threshold cycle (Ct) results of a multiplex QPCR assay and the standard curves generated for purposes of quantification of divIVA and icaA based on 10-fold serial dilutions of *Staphylococcus epidermidis* in platelets according to an embodiment of the subject matter herein described.

FIG. 3B illustrates amplification plots and indicates limits of detection for *Staphylococcus epidermidis* divIVA achieved with QPCR amplification according to an embodiment of the subject matter herein described.

FIG. 4 illustrates Multiplex QPCR amplification by agarose gel visualization of preferred gene targets of *Staphylococcus epidermidis* according to an embodiment of the present subject matter.

DETAILED DESCRIPTION

Figure 1:
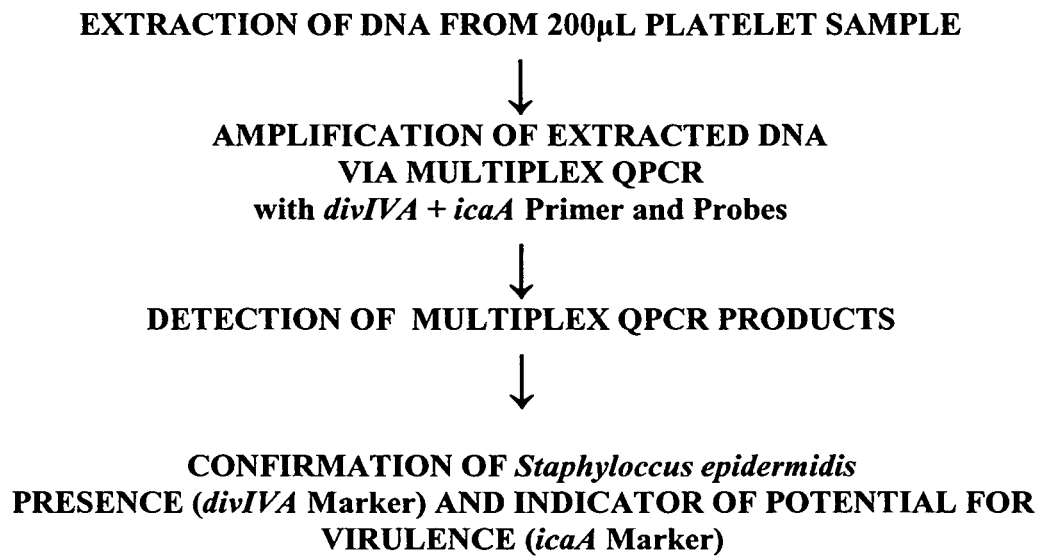
FIG. 1 is a flowchart that illustrates an exemplary process, consistent with an embodiment of the present subject matter for both quantitative and qualitative detection of a *Staphylococcus epidermidis* isolate in a platelet sample using QPCR.

The following detailed description refers to the accompanying drawings. Embodiments of the present subject matter provide means for the efficient and sensitive detection and characterization of *Staphylococcus epidermidis* in samples by performing an optimized PCR method with novel oligonucleotide primers, and corresponding probes. Preferably, according to embodiments of the subject matter provided characterization of a *Staphylococcus epidermidis* may include parameters for detecting quantitative and/or qualitative information about a *Staphylococcus epidermidis* isolate detected. For example, specific genetic markers of relevance have been identified and corresponding detection tools developed to detect, quantify and qualify a *Staphylococcus epidermidis* isolate in a sample of interest. In one such embodiment, means to detect an indicator of bacterial virulence is provided. Thus, the subject matter herein provides a highly sensitive detection protocol for both detecting the presence of this bacteria and also identifying genetic indicators of concern. According to aspects of the present subject matter, potential virulence of *Staphylococcus epidermidis* is one such genetic indicator of concern. Thus, an indicator of bacterial virulence as herein referenced is intended to include an indicator of the potential for virulence in *Staphylococcus epidermidis*. As discussed further herein below, icaA detection is provided as a means to improve the specificity of detection of *Staphylococcus epidermidis* in accordance with embodiments here provided, and as well, is employed to qualify a potential for virulence in *Staphylococcus epidermidis* isolates detected with the same.

Bacterial contamination of blood is of paramount concern in the realm of transfusion medicine. Superior screening methodologies are essential to ensuring the safety of therapeutic blood products. Due to the ever increasing demand for blood products, and the evident limitations to supply, a growing need exists for highly sensitive detection methods which require limited sample sizes for screening purposes. Furthermore, detection methods that can be rapidly executed will improve the availability and preservation of high quality blood products. *Staphylococcus epidermidis* causes 50-70% of nosocomial bloodstream infections originating from the patient's microflora, hospital environment or contaminated blood transfusions. Fatal transfusion reactions due to platelets contaminated with *Staphylococcus epidermidis* have been reported in Canada, the United States and Europe. *Staphylococcus epidermidis* grows slowly in platelets as compared to other bacteria, making its detection by currently used culture methods more challenging. In healthy hosts, *Staphylococcus epidermidis* is a normal inhabitant of skin and mucous membranes. However, in immuno-compromised patients and in those with implanted biomedical devices, this bacterium can become pathogenic. Several *Staphylococcus epidermidis* strains display the ability to form biofilms and biofilm production by these strains and is an indicator of a potential virulent phenotype. For example, infections with *Staphylococcus epidermidis* strains associated with the ability of this organism to form biofilms tend to be more chronic than acute becoming a septic focus, and in some cases leading to death. Thus, it is beneficial to detect an indicator of this potential for virulence when screening for *Staphylococcus epidermidis* in a sample of interest. A genetic marker for icaA is provided in accordance with the present subject matter. In addition, genetic tools and products, including primers and probes, for detecting the presence of icaA in a *Staphylococcus epidermidis* isolate are provided. Accordingly, icaA may serve asian indicator of the potential for virulence of a *Staphylococcus epidermidis* isolate and as a result, provides a means for qualifying the potential for virulence of a *Staphylococcus epidermidis* isolate in accordance with the present subject matter.

The present subject matter provides a rapid and highly sensitive detection method for the detection and quantification of bacterial contamination in a blood product or sample. The method of the present invention provides advantages in time-efficiency, detection sensitivity, quantification capacity and sample size. Thus, the present subject matter provides a convenient and effective screening tool adaptable for a plurality of blood products. In addition to providing a novel detection method, the present subject matter also encompasses products and commercial packages or kits including the same for use in achieving detection of one or more bacterial contaminants of interest. The preferred method, as herein described is a PCR-based assay, however it is fully contemplated that the products employed in accordance with this preferred method can be used in accordance with other molecular detection platforms, including other PCR detection methods known in the art.

According to a preferred aspect of the present invention, a novel detection method adapted to detecting and quantifying *Staphylococcus epidermidis* in a platelet sample is provided, as exemplified in FIG. 1. The method and/or products as described herein for preferred use in detecting *Staphylococcus epidermidis* in a platelet sample may be employed for use in the detection of bacterial contamination in a plurality of blood products and/or samples. A blood sample according to embodiments of the present invention may be whole blood, a component of whole blood, including platelets, red blood cells, granulocytes and plasma, for example or a prepared blood product, such as a buffy coat preparation, for example. Products having specificity for the bacterial contaminants of interest and employed in accordance with the methods of detection of the present invention are also herein provided.

According to a preferred embodiment, bacterial contamination in a blood product or sample is detectable at levels of $10^2$-$10^3$ cfu/ml according to embodiments of the present subject matter. One embodiment provides a rapid and reliable detection method for the bloodborne contaminant *Staphylococcus epidermidis*. According to additional preferred embodiments of the present invention tools specific for detecting and characterizing potentially virulent strains of *Staphylococcus epidermidis* from non-virulent strains are provided.

According to a preferred embodiment of the present invention, there is provided a novel detection method for the rapid and highly sensitive detection of *Staphylococcus epidermidis* in platelets. The sensitivity of this method provides for accurate bacterial detection with a platelet sample of 200 µl whereby detection of $\leq 10^2$ cfu/ml can be achieved within approximately three hours. As a result, rapid, highly sensitive detection and characterization of a very important bloodborne pathogen is achieved.

According to a method of the present subject matter, a 200 µl sample of blood or a blood product, such as platelets for example, can be employed for the purpose of screening for and detecting bacterial contamination therein, instead of the 4 ml need by the currently popular BacT/ALERT™ system. High sensitivity is achieved by the present invention with detection of $10^2$-$10^3$ cfu/ml within approximately three to four hours instead of the 20 hours required by the BacT/ALERT system. This unique method permits the rapid and sensitive detection and characterization of a very important bloodborne pathogen, as further demonstrated by examples herein below.

Nucleic Acid Targets

The cell division gene divIVA of *Staphylococcus epidermidis* (ATCC 700562) was identified as a genetic target for detection of *Staphylococcus epidermidis* contamination in blood which could differentiate the detection of *Staphylococcus epidermidis* from other staphylococcal species. The divIVA gene, which is part of the division cell wall (dcw) cluster of Gram positive cocci including *Streptococcus pneumoniae* and *Enterococcus faecalis*, has been implicated in controlling cell division site selection and chromosome segregation in these organisms (Fadda et al. Journal of Bacterioliology, 2003, Vol. 185, p. 6209-6214; Ramirez-Arcos et al. Microbiology, 2005, vol 151, p. 1381-1393). However, divIVA does not seem to have an important role in cell morphology or chromosome segregation in *Staphylococcus aureus* although it may be involved in septum formation (Pinho and Errington, FEMS Microbiology Letters, 2004, Vol. 240 p. 145-149). Recent studies have shown fundamental differences in genome content and organization between *Staphylococcus aureus* and *Staphylococcus epidermidis* (Zhang et al., Molecular Microbiology, 2003, Vol. 49, p. 1577-1593). Our investigation revealed significant differences in sequence homology between DivIVA proteins from *Staphylococcus aureus* and *Staphylococcus epidermidis* and growth patterns between the two staphylococcal species (FIG. 2A). Further, we have obtained evidence that divIVA is involved in cell division in *Staphylococcus epidermidis* and thus a location within the divIVA gene was selected as a gene target/genetic marker for detection of this bacterium, in accordance with the present subject matter.

The icaA gene was also identified as a potential virulence target for *Staphylococcus epidermidis* and a preferred region thereof was investigated as a genetic marker for characterizing virulence, or the potential for virulence of this bacterium in accordance with an embodiment of the subject matter herein described. Virulent strains of *Staphylococcus epidermidis* grow as biofilms. Bacterial biofilms constitute a community of microorganisms associated with solid-liquid or air-liquid interfaces typically enclosed in an extracellular matrix, with networks of intervening water channels and multiple layers of cells. The cell to cell adhesion phase of *Staphylococcus epidermidis* biofilms involves multiple factors including the polysaccharide intercellular adhesin (PIA). Enzymes involved in the synthesis of PIA are encoded by the intercellular adhesion ica locus containing the icaA, icaD, icaB, and icaC genes. IcaAD has glycosyltransferase activity, whereas IcaC appears to be involved in externalization of the growing polysaccharide and IcaB is involved in PIA modification. *Staphylococcus epidermidis* isolates of clinical relevance (i.e., biologically virulent isolates) are more likely to carry the ica locus than saprophytic strains (Rohde et al., Journal of Clinical Microbiolology, 2004, Vol. 42, p. 5614-5619). Therefore the ica genes, and preferably the icaA gene, have been identified in accordance with the present subject matter as indicators of the invasive potential of isolates of *Staphylococcus epidermidis*. Accordingly, where an indicator of icaA is detected in an embodiment of the present subject matter, a potential for virulence of the *Staphylococcus epidermidis* isolate can be identified. This may be particularly useful information in the field of medical technologies and therapies, and could be the basis for further investigation and/or a corresponding course of action.

Primer Design and Probe Preparation

According to embodiments of the present subject matter, a primer pair and a hydrolysis probe were designed to amplify selected gene targets within internal region of *Staphylococcus epidermidis* divIVA that was determined to be unique to this bacterial species. In addition, internal sequences of the virulence gene icaA have been determined as targets, which allow for differentiation of virulent from non-virulent *Staphylococcus epidermidis* isolates. Thus, according to one embodiment of the present subject matter a multiplex detection system capable of both detecting and characterizing the virulence of *S. epidermidis* bacteria in blood samples is provided.

*Staphylococcus epidermidis* sequences were obtained from GenBank and compared against all other sequences available on-line with Basic Local Alignment Search Tool algorithm (BLAST, National Center for Biotechnology Information, National Institutes of Health). All primers and probes were designed, analysed and selected with the assistance of the following bioinformatics websites:

Primers and probes were designed based on several criteria. Preferred length was determined to be between 18 and 30 nucleotides with a GC content of 40-60%. GC content determines the melting temperature (Tm) of the primers and probes. Ideally the Tm of the probe should be 10° C. higher than the Tm of the primers. Runs of 3 or more Gs or Cs, and mismatches and a T should be avoided at the 3' end. Preferably, primers and probes should not contain complementary sequences. Although it is recommended that amplified DNA fragments are 60-150 bp long, these criteria may need to be relaxed in order to target a specific gene region. Hydrolysis probes for each gene target were dually labelled with fluorescent report and quencher dyes.

These nucleic acid detection tools of the present subject matter, i.e. primers and probes have been incorporated into a methodology for detecting and characterizing *Staphylococcus epidermidis* contamination. It is intended that modifications can be made to these nucleic acid detection tools without deviating from the scope of the subject matter herein provided. For example, fragments and/or functional variants of the nucleic acid products disclosed herein are intended to be encompassed by the scope of the present subject matter. It is contemplated that fragments and/or functional variants of the primers and/or probes herein described can be used in accordance with the methods herein provided to achieve a common objective pursuant to the present subject matter. For example, a fragment or a functional variant of a primer or probe of the present subject matter which retains a similar function such that it may be employed in the detection of *Staphylococcus epidermidis* is intended to be encompassed by the present subject matter. A fragment may include a sequence comprising any number of nucleotides that is less than that found in another nucleic acid sequence of interest, as herein provided. The specificity of a nucleic acid product as herein provided, is intended to refer to the ability of the product, i.e. a primer or probe, for example to anneal to a target region or sequence as the case may be, under conditions suitable for conducting a polymerase chain reaction. It is fully contemplated that the nucleic acid detection tools and methodologies as herein disclosed may be tailored for use in accordance with biological samples, other than blood or blood components which provide a source for bacterial contamination with *Staphylococcus epidermidis*.

Cell division gene divIVA. Although bacterial cell division gene sequences contain variable regions that permit species discrimination, they are highly conserved (usually identical) within isolates of the same species. Therefore, the cell division gene divIVA was selected as a target to develop a PCR detection method for specific detection of *Staphylococcus epidermidis* contamination in platelets.

A 161 bp fragment located at nucleotide position 382 to 542 of the cell division gene *Staphylococcus epidermidis* divIVA (ATCC 700562) was identified as a preferred target region for *Staphylococcus epidermidis* detection, in accordance with the present subject matter. The following primers were prepared, as described above, for use in PCR amplification of the divIVA region of interest:

```
SepdivFW3
5'-TTCCGCTCTCGTTTCCGT-3'        [SEQ ID NO. 1]

RTSepdivREV
5'-ATTGCACGTTCTTCAGGTGT-3'      [SEQ ID NO. 2]
```

The following dual labelled hydrolysis (TaqMan) probe located at nucleotide position 401 to 430 was also prepared for hydrolysis detection of the 161 bp fragment of divIVA above:

```
SepdivProbe
                                 [SEQ ID NO. 3]
5'-FAM-TGCTTGTTGAAGCACAACTTGACTTACTCA-BHQ1-3'
```

The target region for divIVA was compared between two staphylococcal species, *Staphylococcus epidermidis* and *Staphylococcus aureus* using BLAST analysis. This analysis revealed that these regions are 74% identical (FIG. 2A).

Virulence Gene icaA.

The icaA gene is part of the icaADBC gene cluster that is involved in biofilm formation by *Staphylococcus epidermidis*. Therefore, using the icaA gene as a virulence marker allows for selectively discriminating potentially invasive from contaminant *Staphylococcus epidermidis* strains.

A 181-bp fragment located at nucleotide position 739 to 919 of the virulence gene *Staphylococcus epidermidis* icaA was identified as a preferred target region for detecting *Staphylococcus epidermidis* potential virulence in accordance with the present invention. The following primers were prepared, as herein described, for use in PCR amplification of the target icaA region above, according to embodiments of the present invention:

```
QPCRSepiIcaA forward:
5'GCTCTATGCTGGATGTTAGTGCCTGA3'  [SEQ ID NO. 4]

QPCRSepiIcaA reverse:
5'CGATGTAGACCCATGTAATCGATGCG3'  [SEQ ID NO. 5]
```

The following dual labelled hydrolysis (TaqMan) probe located at nucleotide position 1541 to 1566 was also prepared for detection of the 181 bp icaA fragment above:

```
SepiIcaADProbe:
                                 [SEQ ID NO. 6]
5'-HEX-TGGAAACAAAGGGTTCGATGGGCTC-3'-BHQ2
```

The target region for icaA was compared between two staphylococcal species, *Staphylococcus epidermidis* and *Staphylococcus aureus* using BLAST analysis. This analysis revealed a percentage of identity of 83% between the two species (FIG. 2B).

Internal control. A conserved region of the eight currently known alleles of the HLA-DQA1(HLA-DQα1) locus, which is present in residual white blood cells in leukoreduced platelets, was selected as an internal control for our QPCR assays. The use of this 216 bp fragment of the DQα1 gene for similar purposes is exemplified in Mohammadi et al, Transfusion, 2004, Vol. 44, p. 1314-1318, the teachings of which are herein incorporated by reference. The PCR-amplification of HLA-DQα1 has been previously demonstrated to be reproducible and consistent in platelet samples containing at least $1.5 \times 10^4$ white blood cells/300 ml platelet unit.

Primers and probes were synthesized by Integrated DNA Technologies (Coralville, Iowa), based on the parameters outlined above. Once the lyophilized primers were received from the manufacturer, they were reconstituted in nuclease-free water to make a stock of 100 μM. The probe was reconstituted in TE buffer (10 mM Tris, 1 mM EDTA, pH 8.0) to make a stock of 25 μM. Primers and probe were stored at −20° C. in the dark. Primer and probe concentration were optimized, according to Table 1 (below) with control DNA from the target organism.

PCR

A PCR protocol was developed according to the present subject matter to detect and/or quantify the presence of a target nucleic acid sequence in a sample of interest. More preferably, a quantitative PCR or QPCR method is provided. Detection methods employing PCR in accordance with the present subject matter are exemplified herein below. It is fully contemplated that modifications to such methods can be made, without deviating from the scope of the subject matter herein provided in accordance with standard procedures known in the art, and as exemplified Sambrook J et al. 2000. Molecular Cloning: A Laboratory Manual (Third Edition) the teachings of which are herein incorporated by reference. As such, primers developed in accordance with the present subject matter for use in a PCR method are provided to anneal to a target nucleic acid sequence, if that target is present in a sample tested. In doing so, PCR parameters such as annealing temperature and primer and probe concentration were optimized, as illustrated further herein below (Table 1). Subsequently, amplification steps were carried out in accordance with the PCR protocol employed. A quantitative PCR (QPCR) protocol according to an embodiment of the present subject matter includes a fluorescence reporter molecule or probe, and quantification can be determined based on fluorescence intensity. For example, fluorescence data can be collected after the amplification step(s) have been completed, which typically includes 30 to 50 cycles of PCR amplification, and used to determine the quantity of the target present prior to the PCR reaction.

According to a further embodiment of the present invention, the PCR protocol herein provided is adaptable as a multiplex platform for the detection of more than a single nucleic acid target of interest. As exemplified herein below, the present invention may include simultaneous detection of at least two nucleic acid targets, together with appropriate controls. According to a preferred embodiment, a target nucleic acid sequence specific to a bacterial target of interest, as well as a virulence target sequence is provided in accordance in a single assay. In doing so, the present subject matter provides a novel platform for determining preferred characteristics of contaminants of interest.

Furthermore, the present subject matter provides a platform for use in the preparation of a multiplex detection assay for rapidly and reliably detecting a plurality of blood borne bacterial contaminants. Preferably, a multiplex detection method of the present invention provides a platform for the simultaneous detection of *S. epidermidis*, together with other clinically relevant bacterial contaminants of blood samples and products in a single assay, such as for example *Bacillus* spp., *Escherichia coli, Pseudomonas* spp. In particular, a multiplex detection method of the present invention may provide a platform for the detection of one or more indicators of *Staphylococcus epidermidis* contamination simultaneous with the detection of an indicator(s) specific to the presence of other bacteria. A platform of the present subject matter may also be adapted to include other indicators for the characterization of contaminants relevant to the objectives of a detection protocol. More preferably, a multiplex method and assay of the present invention provides means to detect the most clinically relevant bacterial contaminants of blood samples and products in a single assay so as to provide a reliable and improved method for screening thereof.

TABLE 1

Optimization of Multiplex Assay to detect *Staphylococcus epidermidis* divIVA and icaA and the internal control DQα1.

| Assay | Primer concentration (μM) | | Probe concentration | |
|---|---|---|---|---|
| | Range | Optimal | Range | Optimal |
| QPCR to amplify divIVA | 0.5-1.0 | 0.5-0.6[a] | 0.2-0.5 | 0.2[a] |
| QPCR to amplify icaA | 0.4-0.8 | 0.6-0.7[a] | 0.2-0.4 | 0.4[a] |
| QPCR to amplify DQα1 (conditions selected based on published data) | ND | 0.9 | ND | 0.3 |
| Multiplex assay with SYBR Green to detect divIVA, icaA and DQα1 | ND | divIVA = 0.5 icaA = 0.6 DQα1 = 0.9 | — | NAp |

TABLE 1-continued

Optimization of Multiplex Assay to detect *Staphylococcus epidermidis* divIVA and icaA and the internal control DQα1.

| Duplex assay in a MX4000 to detect divIVA and icaA. Quantitect Probe PCR kit | ND | divIVA = 0.5 icaA = 0.6 | ND | divIVA = 0.2 icaA = 0.4 |
|---|---|---|---|---|
| Multiplex assay in a MX4000 to detect divIVA, icaA and DQα1. Quantitect Probe PCR kit | ND | divIVA = 0.5 icaA = 0.6 DQα1 = 0.9 | ND | divIVA = 0.2 icaA = 0.4 DQα1 = 0.3 |

| | Primer/probe comparison | Primer/probe optimal |
|---|---|---|
| Multiplex assay in a MX4000 to detect divIVA, icaA and DQα1. Quantitect Multiplex PCR No ROX kit | divIVA = 0.5/0.2 versus 0.2/0.2[b] icaA = 0.6/0.4 versus 0.2/0.2[b] DQα1 = 0.9/0.3 versus 0.2/0.2[b] | 0.2/0.2 0.6/0.4 0.2/0.2 |

[a]Although the genes were detected at all primer and probe concentrations tested, the most sensitive detection was obtained at the optimal concentrations described in the table
[b]0.2 μM was the concentration recommended by the manufacturer of the kit for primers and probes and was compared with previous optimized concentrations
NAp, Not applicable
ND, Not done Materials & Methods
Platelet Preparation The present invention is herein exemplified with platelet samples, however it is fully contemplated that other biological samples may be prepared and screened according to the protocols herein contemplated. A platelet sample may be obtained from a donor, patient or screening subject according to a standard platelet preparation technique, such as apheresis or whole-blood-derived (WBD) platelets. WBD platelets can be prepared by the platelet rich plasma (PRP) method or by the buffy coat method, such as known in the art. With apheresis or plateletpheresis, blood is drawn from the donor into an apheresis instrument, which, using centrifugation, separates the blood into its components, retains the platelets, and returns the remainder of the blood to the donor. The resulting component contains about six times as many platelets as a unit of platelets obtained from whole blood. Platelets can be stored at room temperature for up to five days. According to a preferred embodiment, platelet samples are screened using a method of the present subject matter immediately prior to medical use, such as for transfusion purposes.

DNA extraction

DNA was extracted from platelet samples using the QIAamp® DNA Blood mini kit (Qiagen) with the modification for Gram positive cocci. Two hundred μl of non-spiked or spiked platelets were centrifuged at 5,000 g for 10 min. Supernatant was removed and the pellet was resuspended in 150 μl of filter-sterilized lysozyme solution (20 mg/ml in 20 mM Tris 2 mM EDTA, pH 8.0, 1.2% Triton X100) followed by incubation at 37° C. for at least 30 min. Twenty μl of proteinase K and 200 μl of AL™ lysis buffer (provided in the kit) were added. The mixture was then vortexed and incubated at 56° C. for 30 min followed by incubation at 95° C. for 15 min. The sample was spun briefly followed by the addition of 200 μl of ethanol (96-100%) and a pulse vortex of 15 sec. The sample was spun again and the entire mixture was applied to the QIAamp® spin column followed by centrifugation at 6,000 g/1 min. The column was then placed into a clean collection tube and 500 μl of AW1 wash buffer (provided in the kit) were added followed by centrifugation at 6,000 g/1 min. The column was placed into a clean collection tube and the wash was repeated as before with AW2 wash buffer. The column was spun at 20,000 g/3 min, placed into a clean collection tube and re-spun at 20,000 g/1 min. Finally, the column was placed into a clean RNase-free/DNase-free tube and the lid left open for 1 min at room temperature to allow the ethanol to evaporate. Fifty μl of nuclease-free water are added to the column followed by incubation for 1 min at room temperature and centrifugation at 6,000 g/1 min for final elution of the DNA, which is stored at −20° C.

QPCR Optimizations for *Staphylococcus epidermidis* divIVA Detection

Quantitect® Probe PCR kit (Qiagen) reagents were used according to manufacturer's direction to prepare a QPCR master mix including Quantitect® Probe reagent (contains HotStart™ Taq buffer and polymerase, dNTP, $MgCl_2$). Various symmetric and asymmetric concentrations of the primers (SEQ ID NOS: 1 and 2) ranging from 0.5 μM-1.0 μM and probe (SEQ ID NO: 3) ranging from 0.2 μM to 0.5 μM were added to the QPCR master mix and optimal primer and probe concentrations were determined to be 0.5-0.6 μM of each primer, and 0.2 μM of the probe (Table 1). Two μl (in a final volume of 20 μl) or 5 μl (in a final volume of 25 μl) of template DNA was added to the master mix and amplified in a Light Cycler® 2.0 (Roche), and an MX4000 (Stratagene), respectively.

The cycling parameters were:

| Light Cycler | 95° C. 15 minutes | Slope 20° C./s for one cycle |
|---|---|---|
| | 95° C. 0 minutes | Slope 20° C./s |
| | 58° C. 1 minute 15 seconds | Slope 20° C./s for 50 cycles |
| MX4000 | 95° C. 15 minutes | One cycle |
| | 95° C. 15 seconds | |
| | 58° C. 1 minute 15 seconds | 50 cycles |

Template Preparation:

A 0.5 McFarland Standard (equivalent to $10^8$ cfu/ml) of *Staphylococcus epidermidis* ATCC 12228 or ATCC 700562 was prepared. Ten-fold serial dilutions ($10^7$ cfu/ml to $10^1$ cfu/ml) of the appropriate strain of *Staphylococcus epidermidis* were prepared in platelets. Diluted spiked platelets were incubated at room temperature (RT) for 2 hours under continuous rotation. Two-hundred μl of the diluted spiked platelets were then used for DNA extraction as described above. The diluted spiked platelets were also plated on blood agar in duplicate to determine colony counts (appropriate dilutions are made in trypticase soy broth). Colonies are counted 18 to 24 hours after plating and incubated at 37° C.

The determination of the level of detection, LOD, (cfu/QPCR reaction) was calculated considering the volume of template added per reaction (as outlined above). Using the optimised protocol in 18 independent assays, the LOD was <1 cfu/reaction in four out of the 18 assays, <10 cfu/reaction in 11 out of the 18 assays, 104 cfu/reaction in two out of the 18 assays, and 932 cfu/reaction in one out of the 18 assays. Based on these results, we established the limit of detection as being between $10^2$ and $10^3$ cfu/reaction.

QPCR Optimizations for *Staphylococcus epidermidis* icaA Detection

Quantitect® Probe PCR kit (Qiagen) reagents are used to prepare a QPCR master mix containing Quantitect® Probe reagent (including HotStart Taq buffer and polymerase, dNTP, $MgCl_2$). Various symmetric and asymmetric concentrations of the primers (SEQ ID NOS: 4 and 5) ranging from 0.4-0.8 μM and 0.2-0.4 μM of probe (SEQ ID NO: 6) were added to the QPCR master mix. Optimal primer concentrations were determined to be 0.6-0.7 μM of each primer, and 0.4 μM of the probe (Table 1). Two μl (in a final volume of 20 μl) or 5 μl (in a final volume of 25 μl) of template DNA was added to the master mix and amplified in a Light Cycler® 2.0 (Roche), and/or an MX4000 (Stratagene), respectively.

The cycling parameters were:

| Light Cycler | 95° C. 15 minutes | Slope 20° C./s for one cycle |
|---|---|---|
| | 95° C. 0 minutes | Slope 20° C./s |
| | 58° C. 1 minute 15 seconds | Slope 20° C./s for 50 cycles |
| MX4000 | 95° C. 15 minutes | One cycle |
| | 95° C. 15 seconds | |
| | 58° C. 1 minute 15 seconds | 50 cycles |

Template preparation was done as described for divIVA but strains *Staphylococcus epidermidis* ATCC 35984 or O-47 were used as templates for icaA amplification. In four independent assays, the LOD was determined to be <$10^2$ cfu/reaction.

PCR Detection of the Internal Control Gene HLA DQα1

A 216 bp internal gene fragment present in the eight currently known alleles at the HLA DQα1 locus of the residual white blood cells (WBCs) in leukoreduced platelet units was successfully amplified from platelet samples spiked with *Staphylococcus epidermidis* using the following primers and probe sequences obtained from the published manuscript by Mohammadi T et al., Transfusion, 2004, Vol. 44, p. 1314-1318, which is herein incorporated by reference.

```
                                            (SEQ ID NO: 7)
DQAForward:
5'-TTGTACCAGTTTTACGGTCCC-3'

(SEQ ID NO: 8)
DQAReverse:
5'-TGGTAGCAGCGGTAGAGTTG-3'

(SEQ ID NO: 9)
DQAProbe:
5'Cy5-TTCTACGTGGACCTGGAGAGGAAGGAG-3'BHQ2
```

Quantitect® Probe PCR kit (Qiagen) reagents were used to prepare a QPCR master mix, according to manufacturer's instructions. Concentrations of DQα1 primers and probe were selected at 0.9μM and 0.3μM respectively, based on published data (Mohammadi T et al., Transfusion, 2004, Vol. 44, p.1314-1318). Five μl (in a final volume of 25 μl) of template DNA was added to the master mix and amplified in an MX4000 (Stratagene) quantitative PCR instrument.

The cycling parameters were the same as for the amplification of divIVA and for icaA Template preparation was done as described for icaA amplification (above). Positive PCR results were obtained from DNA extracted from 200 μl samples of 8 individual apheresis platelet units, and 3 human plasma samples. QPCR amplification was performed in triplicate on 8 individually extracted DNA samples originating from one apheresis platelet sample that had been spiked with *Staphylococcus epidermidis* O-47 and serially diluted 10-fold. The average Cp (Crossing point) was 33.27+/−0.628, 33.425+/−0.12 and 32.24+/−0.59 indicating good reproducibility. As a result, the HLA DQα1 gene was selected as a suitable internal control in this assay.

Determination of the LOD of DQα1 in Residual WBCs Contained in the Platelet Samples Initial attempts to determine the LOD of DQα1 in the leukoreduced apheresis platelet unit used for this spiking experiment by flow cytometry resulted in counts of less than 0.05 WBCs/μl (0.05 WBCs/μl is the limit of detection of this system). This may be due to low WBC content in the unit as it was leukoreduced (<0.83 WBC/μl) and/or to breakdown of WBCs in the unit as these were outdated platelets. The detection of DQα1 in this unit was positive by QPCR (as above) likely due to cell-free DNA that served as a template for the QPCR reactions. To overcome the failed WBC quantification by flow cytometry in this leukoreduced platelet unit, a sample of whole blood containing 5,907 WBC/μl (determined by flow cytometry) was used for optimization experiments. DNA was extracted from this unit and used as a template for DQα1 QPCR. The LOD of this assay was determined to be 0.6 WBCs/μl. Using serial dilutions of the DNA extracted from whole blood, a DQα1 QPCR standard curve was prepared. The WBC content of four outdated platelet units was calculated against this standard curve and found to range from 1.9 to 8.7 WBC/μl. Only the unit containing 8.7 WBC/μl yielded positive results in flow cytometry assays (1 WBC/μl).

Multiplex Assay Detection of *Staphylococcus epidermidis* Using divIVA, icaA and the Internal Control DQα1 Gene Primers and Multiplex QPCR Assay in a Light Cycler®2.0 System Primers at the optimal concentrations described above, and exemplified in Table 1 were employed together with Light Cycler® Fast Start DNA Master$^{pLUS}$ SYBR Green 1 kit reagents, according to manufacturer's instructions, to prepare a master mix to amplify the three target genes from spiked platelet DNA according to a multiplex PCR platform according to the present subject matter. Four μl of SYBR Green master mix were added to a final volume of 20 μl containing primers for the three genes, divIVA, icaA and DQα1 at the optimized concentrations, followed by the addition of 5 μl of template DNA.

All three gene targets were amplified in the Light Cycler® 2.0 using the following cycling parameters:

| 95° C. | 10 minutes | Slope 20° C./s | One cycle |
|---|---|---|---|
| 95° C. | 10 seconds | Slope 20° C./s | |
| 58° C. | 10 seconds | Slope 20° C./s | |
| 72° C. | 05 seconds | Slope 20° C./s | 50 cycles |

Followed by a melting curve program

| 95° C. | 0 seconds | Slope 20° C./s | |
|---|---|---|---|
| 60° C. | 15 seconds | Slope 20° C./s | |
| 95° C. | 05 seconds | Slope 0.2° C./s | One cycle |

Data was acquired using the step mode

The amplicons were analysed-using the Light Cycler®2.0 software and visualized on an agarose gel (data not shown).

The LOD for divIVA was 22 cfu/reaction and 220 cfu/ml for icaA. DQα1 was detected in samples containing $10^1$-$10^5$ cfu/ml and in non-spiked platelet DNA. These results illustrate that the these three genes can be detected together in a QPCR multiplex assay according to the present subject matter.

divIVA and icaA Duplex QPCR Assay in a MX4000 System (Stratagene™)

The divIVA and icaA genes have been successfully amplified from *Staphylococcus epidermidis* strain O-47 in a duplex QPCR reaction using the Quantitect® PCR Probe kit (Qiagen) reagents, according to manufacturer's instructions, with the addition of optimal primer and probe concentrations as described herein above. Quantitect® Probe PCR kit (Qiagen) reagents are used to prepare a QPCR master mix containing: 12.5 μl of 2× Quantitect® Probe reagent (including HotStart Taq buffer and polymerase, dNTP, MgCl$_2$), divIVA primers and probe at concentrations of 0.5 μM and 0.2 μM, respectively, icaA primers and probe at concentrations of 0.6 μM and 0.4 μM, respectively, 5 μl of template DNA and nuclease-free water for a final volume of 25 μl, followed by amplification in a MX4000 instrument (Stratagene)(Table 1).

The cycling parameters were:

| 95° C. | 15 minutes | One cycle |
|---|---|---|
| 95° C. | 15 seconds | |
| 58° C. | 1 minute 15 seconds | 50 cycles |

Results

The LOD was 2.25 cfu/reaction for both targets.

divIVA, icaA and DQα1 Multiplex QPCR Assay in a MX4000 System (Stratagene™)

The divIVA, icaA and DQα1 genes have been successfully amplified from DNA templates extracted from apheresis platelets spiked with *Staphylococcus epidermidis* strain O-47 in a multiplex QPCR reaction using the Quantitect® Probe PCR kit (Qiagen), according to manufacturer's instructions. Quantitect® Probe PCR kit (Qiagen) reagents are used to prepare a QPCR master mix containing: 12.5 μl of 2× Quantitect® Probe reagent (including HotStart Taq buffer and polymerase, dNTP, MgCl$_2$), divIVA primers and probe at concentrations of 0.5 μM and 0.2 μM, respectively, icaA primers and probe at concentrations of 0.6 μM and 0.4 μM, respectively, DQα1 primers and probe at concentrations of 0.9 μM and 0.3 μM, respectively, 5 μl of template DNA and nuclease-free water for a final volume of 25 μl, followed by amplification an MX4000 (Stratagene).

The following cycling parameters were used in the MX4000 QPCR instrument:

| 95° C. | 15 minutes | One cycle |
|---|---|---|
| 95° C. | 15 seconds | |
| 58° C. | 1 minute 15 seconds | 50 cycles |

Additional 0.35 units of HotStar Taq DNA polymerase was added to the master mix for each QPCR reaction when a multiplex assay was set.

The LOD was 22 cfu/reaction for divIVA and <0.2 cfu/reaction for icaA. The average Cp for DQα1 was 35.13+/−0.383 for the multiplex assay and 33.59+/−2.5 for the single target assay. These results illustrate the effectiveness of an optimized multiplex QPCR assay to detect the two staphylococcal gene targets and that DQα1 can be used as an internal control.

Validation of the Multiplex QPCR Assay by Different Operators Using Quantitect® Probe PCR Kit Two experiments were run to validate the optimized Multplex QPCR method of the present subject matter, as described above. Three separate operators spiked outdated apheresis platelet units with *Staphylococcus epidermidis* O-47, diluted the material from $10^7$ to $10^1$ cfu/ml and extracted DNA from each dilution in duplicate according to the protocol described previously. Trypticase soy broth (TSB) media and non-spiked platelets were used as negative controls for the extraction. Subsequently, one operator set up three separate QPCR assays using each of the three sets of DNA in triplicate. Water was used as a negative control for the QPCR. Spiking and extraction was repeated by two operators and the DNA assayed in triplicate using the same negative controls.

Results

The LOD for divIVA and icaA varied between 2-22 cfu/reaction in all of the QPCR assays conducted. Positive results were obtained for divIVA in some of the TSB and non-spiked platelet samples. These negative controls becoming positive at the end of the run cycles invalidated any result with a concentration equal or <2 cfu/reaction. Therefore, the minimal LOD of this assay was determined to be 22 cfu/reaction. Detection of DQα1 was positive as expected in samples containing low bacterial concentrations. Negative DQα1 detection at higher bacterial concentrations is due to competition for PCR amplification of the other bacterial targets divIVA and icaA.

Validation of the Multiplex QPCR Assay Using QuantiTect® Multiplex PCR No ROX Kit Assay A QuantiTect® Multiplex PCR No ROX kit (Qiagen) was employed according to manufacturer's recommended instructions to validate the results obtained with the previously optimized multiplex assay. DNA extracted from one of the previous assays was used in duplicate for this experiment. Previously optimized primer and probe concentrations (Table 1) were compared with those recommended by the kit manufacturer (0.2 μM each primer and 0.2 μM probe), using the manufacturer's recommended cycling conditions:

| | | |
|---|---|---|
| 95° C. | 15 minutes | One cycle |
| 94° C. | 1 minute | |
| 58° C. | 1 minute 30 seconds | 50 cycles |

The temperature for the combined annealing/extension step was decreased from 60° C. (recommended by manufacturer) to 58° C.

Results

Using optimized primer and probe concentrations as outlined in Table 1, the negative controls (non-spiked TSB and platelets) had a negative result for divIVA, and the LOD was 2 cfu/reaction for both divIVA and icaA. Detection of DQα1 was positive as expected in samples containing lower bacterial concentrations (i.e., $10^7$ cfu/ml) as illustrated in FIG. 4. Negative DQα1 detection at higher bacterial concentrations (i.e., $10^8$ cfu/ml) is due to competition for PCR amplification of the other bacterial targets divIVA and icaA. As illustrated in FIGS. 3A and 3B, standard curves as obtained for S. epidermidis divIVA (blue) and S. epidermidis icaA (green), with this protocol are provided. FIG. 3A illustrates threshold cycle (Ct) results of a multiplex QPCR assay and the standard curves are provided for determining quantification of divIVA and icaA based on 10-fold serial dilutions of Staphylococcus epidermidis in platelets, in accordance with the present subject matter. In addition, FIG. 3B illustrates amplification plots and indicates limits of detection for Staphylococcus epidermidis divIVA achieved with QPCR amplification according to an embodiment of the subject matter herein described. DNA was extracted from spiked platelets with $10^1$-$10^8$ cfu/ml. Curves for divIVA (blue) and icaA (green) overlap showing linearity between $10^2$-$10^8$ cfu/ml with PCR efficiencies of 95.5% and 94.4%, respectively. The QuantiTect® Multiplex PCR No ROX kit was employed to successfully eliminate positive detection of divIVA from negative control samples and therefore in increasing the level of sensitivity for divIVA and icaA in this assay from 22 cfu/reaction to 2 cfu/reaction, which corresponds to platelet samples spiked with $10^2$ cfu/ml (FIGS. 3B and 4).

A QuantiTect® Multiplex PCR No ROX kit provides an exemplary QPCR protocol for employing the present subject matter to provide a multiplex platform for the simultaneous detection of the genetic markers provided for detecting Staphylococcus epidermidis contamination, and characterizing a potential for virulence of the Staphylococcus epidermidis strain together with a suitable control. According to the present subject matter genetic markers for divIVA, icaA, and DQαI are employed in a multiplex PCR protocol, such as that exemplified in QuantiTect® Multiplex PCR No ROX kit, and further optimized as herein described (Table 1) for detecting and characterizing Staphylococcus epidermidis in a blood sample. Using the QuantiTect® Multiplex PCR No ROX kit as an exemplary PCR platform, the multiplex detection of these three gene targets was optimized and false positive results were eliminated. Thus, a multiplex PCR protocol for detecting and characterizing Staphylococcus epidermidis contamination in platelets is hereby established with the subject matter herein disclosed. It is fully contemplated that the products and methods of the present subject matter may be adaptable for use with DNA extracted from other biological samples and preparation according to known procedures to be employed successfully in the multiplex detection of the gene targets described herein.

Specificity Assays

Staphylococcus epidermidis divIVA

To verify the specificity of the QPCR amplification of Staphylococcus epidermidis divIVA according to the present subject matter, specificity assays using the Quantitect® Probe PCR Kit and the Light Cycler®2.0 system according to manufacturer's recommended instructions, were conducted with the divIVA genetic marker herein described. QPCR amplification was positive in four Staphylococcus epidermidis strains and negative in seven Staphylococcus aureus strains, in two Staphylococcus xylosus strains, and in one Staphylococcus saprophyticus strain.

Staphylococcus epidermidis icaA

To verify the specificity of the QPCR amplification of Staphylococcus epidermidis icaA according to the present subject matter, specificity assays using the Quantitect® Probe PCR Kit and the Light Cycler®2.0 system were conducted with an icaA genetic marker as herein described. QPCR amplification of Staphylococcus epidermidis icaA was positive in three biofilm forming (virulent) Staphylococcus epidermidis strains and negative in three biofilm negative Staphylococcus epidermidis, seven Staphylococcus aureus strains, in two Staphylococcus xylosus strains, in one Staphylococcus capitis strain, and in one Staphylococcus saprophyticus strain.

It is contemplate that the subject matter herein described may be adapted to provide a multiplex QPCR method that detects Staphylococcus epidermidis in blood components other than platelets. Other blood components which may preferably be screened for Staphylococcus epidermidis contamination may include plasma, plasma protein fractions, serum, whole blood, or red blood cells, for example. In addition, the present subject matter may also be adapted for use in screening other biological samples from which DNA can be extracted for the purpose of screening for the presence of Staphylococcus epidermidis contamination therein.

For example, extraction of DNA from the blood component using a Qiagen™ DNA Blood kit according to manufacturer's recommended instructions, for example could be provided with possible modification as required to extract DNA from Gram positive bacteria. A multiplex QPCR assay as per the method herein above to detect the presence of the *Staphylococcus epidermidis* divIVA and icaA genes, and a suitable internal control, such as HLA DQα1, for example. However, it should be noted that the detection of the HLA DQα1 gene that has been used as an internal control for the detection of *Staphylococcus epidermidis* in platelets, will only be possible if a minimal number of residual white blood cells in the blood component is present. This minimal number would initially need to be validated for each component being tested. Any component not consistently containing the minimal number of residual white blood cells necessary for detection would necessitate the inclusion of an alternate internal control to confirm adequate extraction and absence of PCR inhibition. For other blood samples or components, an alternative internal control marker may be selected. Once an internal control is chosen, validation of the method could be performed, by performing three separate DNA extractions and PCR amplifications by three operators on three separate trials, for example.

It will be understood that various details of the claimed subject matter can be changed without departing from the scope of the claimed subject matter. Furthermore, the foregoing description is for the purpose of illustration only, and not for the purpose of limitation.

The invention claimed is:

1. A method for detecting *Staphylococcus epidermidis*, said method comprising:
   isolating DNA from a sample suspected of containing *Staphylococcus epidermidis*;
   subjecting the DNA to a polymerase chain reaction amplification utilizing a first primer pair, wherein said first primer pair is specific for a region of a divIVA gene of *Staphylococcus epidermidis* wherein said first primer pair comprises a first primer of (SEQ ID NO:1) 5'TTC-CGCTCTCGTTTCCGT3' base sequence and a second primer of (SEQ ID NO:2) 5'ATTGCACGTTCTTCAG-GTGT3' base sequence; and
   detecting *Staphylococcus epidermidis* by detecting the amplification product of the polymerase chain reaction.

2. The method of claim 1 wherein said detecting includes visualizing or quantifying the product of the polymerase chain reaction.

3. The method of claim 1 wherein the polymerase chain reaction is a quantitative polymerase chain reaction.

4. The method of claim 3 wherein subjecting the DNA to quantitative polymerase chain reaction includes utilizing a probe having specificity to the amplification product of the first primer pair.

5. The method of claim 4 wherein said probe comprises a base sequence (SEQ ID NO. 3) 5'-FAM-TGCTTGTTGAAG-CACAACTTGACTTACTCA-BHQ1-3'.

6. The method of claim 1 wherein the polymerase chain reaction is a multiplex polymerase chain reaction for detecting and characterizing *Staphylococcus epidermidis*; and subjecting the DNA to the multiplex polymerase chain reaction further utilizes at least one primer of a second primer pair specific to a region of an icaA gene of *Staphylococcus epidermidis*.

7. The method of claim 6 wherein said at least one primer of the second primer pair comprises one of a (SEQ ID NO. 4) 5'GCTCTATGCTGGATGTTAGTGCCTGA3' base sequence and (SEQ ID NO. 5) 5'CGATGTAGACCCATGTAATCGATGCG3' base sequence.

8. The method of claim 6 wherein said second primer pair comprises a first primer of a (SEQ ID NO. 4) 5'GCTCTATGCTGGATGTTAGTGCCTGA3' base sequence and a second primer of a (SEQ ID NO. 5) 5'CGATGTAGACCCATGTAATCGATGCG3' base sequence.

9. The method of claim 6 wherein characterizing *Staphylococcus epidermidis* includes detecting a second product of the polymerase chain reaction corresponding to said at least one second primer specific to a region of an icaA gene wherein said second product provides an indicator of potential *Staphylococcus epidermidis* virulence.

10. The method of claim 6 wherein subjecting the DNA to the multiplex polymerase chain reaction includes utilizing a second probe having specificity to the amplification product of the at least one primer of the second primer pair.

11. The method of claim 10 wherein the probe comprises a base sequence (SEQ ID NO:6) 5'-HEX-TGGAAACAAAGGGTTCGATGGGCTC-3'-BHQ2.

12. The method of claim 1 wherein said sample is a blood sample.

13. The method of claim 12 wherein the blood sample is a platelet sample.

14. A method for simultaneously detecting and characterizing *Staphylococcus epidermidis*, said method comprising:
   isolating DNA from a sample suspected of containing *Staphylococcus epidermidis*;
   subjecting the DNA to a multiplex polymerase chain reaction amplification utilizing a first primer pair having specificity to a divIVA gene target of *Staphylococcus epidermidis* and at least one primer from a second primer pair having specificity to an icaA gene target of *Staphylococcus epidermidis* wherein said first primer pair comprises a first primer of (SEQ ID NO:1) 5'TTCCGCTCTCGTTTCCGT3' base sequence and a second primer of (SEQ ID NO:2) 5'ATTGCACGTTCTTCAGGTGT3' base sequence; and
   screening for products of the polymerase chain reaction for each of the divIVA gene target and icaA gene target of *Staphylococcus epidermidis* to obtain an indication of the presence and phenotype of *Staphylococcus epidermidis* in the sample.

15. The method of claim 14 wherein said at least one primer of the second primer pair is selected from a (SEQ ID NO:4) 5'GCTCTATGCTGGATGTTAGTGCCTGA3' base sequence and a (SEQ ID NO:5) 5'CGATGTAGACCCATGTAATCGATGCG3' base sequence.

16. The method of claim 15 wherein subjecting the DNA to polymerase chain reaction further utilizes a first and a second probe corresponding to said amplification product of said first primer pair and said second primer pair respectively, wherein said first probe comprises a base sequence (SEQ ID NO.3) 5'-FAM-TGCTTGTTGAAGCACAACTTGACTTACTCA-BHQ1-3' and said second probe comprises (SEQ ID NO.6) 5'-HEX-TGGAAACAAAGGGTTCGATGGGCTC-3'-BHQ2.

* * * * *

SEQUENCE LISTING

```
<160> NUMBER OF SEQ ID NOS: 13

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttccgctctc gtttccgt                                                    18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
attgcacgtt cttcaggtgt                                                  20

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: FAM-T
<220> FEATURE:
<221> NAME/KEY: modified_base
<222> LOCATION: (30)
<223> OTHER INFORMATION: A-BHQ1

<400> SEQUENCE: 3
tgcttgttga agcacaactt gacttactca                                       30

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctctatgct ggatgttagt gcctga                                           26
```

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgatgtagac ccatgtaatc gatgcg                                           26

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: HEX-T
<220> FEATURE:
<221> NAME/KEY: modified_base
<222> LOCATION: (25)
<223> OTHER INFORMATION: C-BHQ2

<400> SEQUENCE: 6
tggaaacaaa gggttcgatg ggctc                                            25

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttgtaccagt tttacggtcc c                                                21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggtagcagc ggtagagttg                                                  20

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Cy5-T
<220> FEATURE:
<221> NAME/KEY: modified_base
<222> LOCATION: (27)
<223> OTHER INFORMATION: G-BHQ2

<400> SEQUENCE: 9

-continued

```
ttctacgtgg acctggagag gaaggag                                          27

<210> SEQ ID NO 10
<211> LENGTH: 161
<212> TYPE: DNA
<213> ORGANISM: Staphylococcus epidermidis

<400> SEQUENCE: 10
ttccgctctc gtttccgtat gcttgttgaa gcacaacttg acttactcaa aagtgaagat      60
tgggattact tactcaatta tgatttagac gccgagcaag tgacattaga agatattcat     120
catcttcatg ataatgattt gacacctgaa gaacgtgcaa t                         161

<210> SEQ ID NO 11
<211> LENGTH: 160
<212> TYPE: DNA
<213> ORGANISM: Staphylococcus aureus

<400> SEQUENCE: 11
tttagatcgc gtttccgtat gttagttgaa gcgcaattag acttattaaa aaacgaagat      60
tgggattact tgttgaatta tgatttagac gctgaacaag tgacgcttga aaatattcat     120
catttgcatg aaaatgattt aaagccagat gaagttgcag                           160

<210> SEQ ID NO 12
<211> LENGTH: 181
<212> TYPE: DNA
<213> ORGANISM: Staphylococcus epidermidis

<400> SEQUENCE: 12
gctctatgct ggatgttagt gcctgaaact ataggtggtt tatggaaaca aagggttcga      60
tgggctcaag gcgggcatga agtacttta agagactttt ggccaacaat taaaactaag     120
aaattatcac tatatatttt aatgtttgaa caaatcgcat cgattacatg ggtctacatc    180
g                                                                    181

<210> SEQ ID NO 13
<211> LENGTH: 181
<212> TYPE: DNA
<213> ORGANISM: Staphylococcus aureus

<400> SEQUENCE: 13
gccatgtgtt ggatgttggt tccagaaaca ttgggaggtc tttggaagca acgcgtgaga      60
tgggctcaag ggggacacga agtattacta cgagactttt ttagcacaat gaaaacgaaa    120
aggtttcctt tatatatttt gatgtttgag caaatcatct caattttatg ggtatatata    180
g                                                                    181
```